United States Patent [19]

Ibsen et al.

[11] 4,264,489

[45] Apr. 28, 1981

[54] PROVISIONAL CROWN-AND-BRIDGE RESIN CONTAINING TETRAHYDROFURYL METHACRYLATE

[75] Inventors: Robert L. Ibsen; William R. Glace, both of Santa Maria, Calif.

[73] Assignee: Den-Mat, Inc., Santa Maria, Calif.

[21] Appl. No.: 111,677

[22] Filed: Jan. 14, 1980

[51] Int. Cl.³ .................... C08F 265/06; C08L 33/14
[52] U.S. Cl. ..................... 260/42.52; 260/45.7 R; 260/45.95 R; 525/206; 525/228; 525/259; 525/284; 525/309
[58] Field of Search ............... 525/284, 309, 228, 206; 260/42.52, 45.95

[56] References Cited

U.S. PATENT DOCUMENTS

| | | | |
|---|---|---|---|
| 3,265,768 | 8/1966 | Mottus et al. | 525/284 |
| 3,468,977 | 9/1969 | Bruckmann et al. | 525/309 |
| 4,001,939 | 1/1977 | Gross | 32/15 |

OTHER PUBLICATIONS

Reinhardt—"Improving the Onlay Temporary Restoration", Dental Student, vol. 57, No. 4, Jan. 1979, pp. 54–55.

*Primary Examiner*—Carman J. Seccuro
*Attorney, Agent, or Firm*—Owen, Wickersham & Erickson

[57] ABSTRACT

A provisional crown-and-bridge resin comprising a liquid resin component and a powder component. The liquid resin component contains tetrahydrofurfuryl methacrylate as a major ingredient and is free from methyl methacrylate. It also contains an anti-oxidant and an accelerator. The powder component contains poly (ethyl methacrylate) as a major ingredient and a curing agent for the resin component. The powder is mixed with the resin shortly before application at a ratio of about two to about five parts of powder to one part of liquid resin by weight, to give a suitably flowing mixture. The resin component may also contain ethyl methacrylate as a major ingredient and may contain ethoxylated bisphenol A dimethacrylate as a major ingredient. The powder may include a substantial proportion of amorphous silica and preferably incorporates a substantial amount of X-ray opaque barium glass.

29 Claims, No Drawings

PROVISIONAL CROWN-AND-BRIDGE RESIN CONTAINING TETRAHYDROFURYL METHACRYLATE

BACKGROUND OF THE INVENTION

This invention relates to a provisional crown-and-bridge resin comprising a powder-liquid restorative system.

Provisional crown-and-bridge resins are used in the mouth after a dentist has prepared the tooth, as a short-term filling-like structure for the patient to use during the time the laboratory is manufacturing the permanent crown or other prosthesis. Typically these resins are supposed to remain in place for several weeks, but may, in some cases, remain for as long as two years or more.

For some time the materials that have been used for temporary crown-to-bridge resins have been based on systems employing methyl methacrylate, for example, systems bases on methyl methacrylate resin and poly (methyl methacrylate) powder in conjunction with a peroxide and amine curing system. These systems have had high cure shrinkages, so that they have tended to pull away from the tooth as they cure.

A more serious difficulty has been that these prior art systems have tended to cause tissue irritation, apparently due to traces of the methyl methacrylate monomer remaining in the cured polymer. These traces may be due to the difficulty of getting an exactly stoichiometric amount of curing agent mixed with the resin or to less-than-perfect mixture of ingredients.

A recent system from Germany described as epimine has very low cure shrinkage, but it also has exhibited gingival irritation, apparently due to some toxic curing agent. This German material has also been somewhat weaker in impact strength than the materials previously used and is very translucent.

In 1978 some new systems appeared that were based on poly (ethyl methacrylate). These systems have been advertised as having low cure shrinkages compared to methyl methacrylate and also a lower exotherm than methyl methacrylate systems. They have not however, solved the gingival irritation problem.

Another problem common to all systems used heretofore has been that they are transparent to X-rays, so that X-ray photographs do not detect their presence. This fact can become very serious if, as is not uncommon, a patient swallows the provisional crown or aspirates it into a lung, for it then becomes impossible to locate the crown with X-rays, or even know whether it is in a lung or in the digestive tract.

Among the objects of the invention are:

To provide an improved provisional crown-and-bridge resin,

To provide a provisional crown-and-bridge resin that does not irritate gingival tissue, To provide a provisional crown-and-bridge resin with very low shrinkage upon cure, To provide a suitably tough and adherent crown-and-bridge resin, and To provide an X-ray opaque crown-and-bridge resin.

SUMMARY OF THE INVENTION

The present invention provides a provisional or temporary crown-and-bridge resin based, in most instances, upon a ethyl methacrylate resin and a poly (ethyl methacrylate) powder. In addition, the material has been made radiopaque by adding barium glass to the poly (ethyl methacrylate) powder.

The resin, usually based on ethyl methacrylate monomer, has a high percentage of tetrahydrofurfuryl methacrylate.

When properly used, this new resin results in very low cure shrinkage. Possibly, the furfuryl ring is somehow opened to effect this desirable result, although the precise reason for the small amount of shrinkage is not completely known at this time. In some forms of the resin, the tetrahydrofurfuryl methacrylate is the sole resin component, except for some minor ingredients, such as anti-oxident, accelerator, etc.

The resin also may contain ethoxylated bisphenol A dimethacrylate as a major component.

Unique properties of this provisional or temporary crown or bridge resin are: (1) very low cure shrinkage, (2) its X-ray opaqueness, (3) little or no gingival irritation, and (4) toughness greater than other provisional crown and bridge resin materials.

The material is easy to handle. It sets into a putty or rubbery stage about 60 seconds to 2½ minutes after activation and sets hard in about 3½ to 6 minutes.

PREFERRED EMBODIMENTS OF THE INVENTION

The invention comprises a liquid or resin and a powder which are mixed in proper proportions, typically in a ratio of about two parts of liquid to seven parts of powder, but this ratio may vary from about two to five parts of powder per part of liquid.

The composition of the liquid resin lies within the following ranges:

| Component | Per cent range, parts by weight |
| --- | --- |
| LIQUID RESIN | |
| Ethyl methacrylate | 0–70.0 |
| Ethoxylated bisphenol A dimethacrylate | 0–40.0 |
| Tetrahydrofurfuryl methyacrylate | 30–60 |
| Antioxidant | 0.01–5 (depending partly on specific antioxident used.) |
| Ultra-violet light absorbing agent | 0–2.0 |
| Cure accelerator | 0.1 to 2.0 (depending partly on specific accelerator used) |
| POWDER | |
| Poly (ethyl methacrylate) | 39–100 |
| Amorphous silica or barium glass | 0–39 |
| Benzoyl peroxide (or other resin curing agent) | enough to cure resin in liquid resin compound |

Shortly before use, the powder is mixed with the liquid to achieve a thick but still favorable consistency, in an amount by weight of two to five parts of powder per part of liquid, typically in the ratio of seven parts of powder to two parts of liquid. The powder may be varied by adding suitable color materials, suitable dyes or pigments so as to match the color of the teeth, especially when used for a portion of a tooth that is to be at the front of the mouth and exposed to viewers. Suitable materials include brown and yellow dyes, titanium dioxide, cadmium sulfide, and black iron oxide, all used in small amounts.

The following examples show various formulations, all figures representing parts by weight:

EXAMPLE 1

|  | Parts by Weight |
|---|---|
| Liquid Resin: | |
| Tetrahydrofurfuryl methacrylate | 60 |
| Ethoxylated bisphenol A dimethacrylate | 40 |
| Butylated hydroxytoluene (anti-oxident) | 0.1 |
| 2-hydroxy-4-methoxybenzophenone (e.g. U.V. 5411) | 2.0 |
| 2-hydroxyethyl-p-toluidine (cure accelerator) | 2.0 |
| Powder: | |
| Poly (ethyl methacrylate) | 98.5 |
| Benzoyl peroxide (as curing agent) | 1.5 |
| Power-to-Resin ratio | 3.5:1.0 |

This composition set hard in two minutes.

EXAMPLE 2

|  | Parts by Weight |
|---|---|
| Liquid Resin: | |
| Tetrahydrofurfuryl methacrylate | 60 |
| Ethoxylated bisphenol A dimethacrylate | 40 |
| Butylated hydroxytoluene | 0.1 |
| 2-hydroxy-p-toluidine | 1.0 |
| 2-hydroxy-4-methoxybenzophenone | 2.0 |
| Powder: | |
| Same as Example 1. | |
| Powder-to-Resin ratio | 3.5:1.0 |

This composition set hard in four minutes, but it went through a cheese-like stage instead of the more desirable rubbery stage.

EXAMPLE 3

|  | Parts by Weight |
|---|---|
| Liquid Resin: | |
| Tetrahydrofurfuryl methacrylate | 60 |
| Ethyl methacrylate | 40 |
| Butylated hydroxytoluene | 0.1 |
| 2-hydroxy-4-methoxybenzophenone | 2.0 |
| 2-hydroxyethyl-p-toluidine | 1.0 |
| Powder: | |
| Poly (ethyl methacrylate) with 1.5% benzoyl peroxide | 50 |
| 90 to 10 mixture of poly (ethyl methacrylate) and poly (methyl methacrylate), without added benzoyl peroxide | 50 |
| Powder-to-Resin ratio: | 3.5:1.0 |

This composition set hard in about six minutes after going through the desired rubbery stage.

EXAMPLE 4

|  | Parts by Weight |
|---|---|
| Liquid Resin: | |
| Tetrahydrofurfuryl methacrylate | 40 |
| Ethyl methacrylate | 60 |
| 2-hydroxyethyl-p-toluidine | 0.5 |
| Powder: | |
| Same as Example 3. | |
| Powder-to-Resin ratio: | 3.5:1.0 |

Cure shrinkage was 0.17% and 0.18%.

EXAMPLE 5

|  | Parts by Weight |
|---|---|
| Liquid Resin: | |
| Tetrahydrofurfuryl methacrylate | 50 |
| Ethyl methacrylate | 50 |
| 2-hydroxyethyl-p-toluidine | 0.3 |
| 2-hydroxy-4-methoxybenzophenone | 2.0 |
| Powder: | |
| Poly (ethyl methacrylate) with 1.5% added benzoyl peroxide | 100 |
| powder-to-Resin ratio: | 3.5:1.0 |

Cure shrinkage was 0.43%.

EXAMPLE 6

|  | Parts by Weight |
|---|---|
| Liquid Resin: | |
| Tetrahydrofurfuryl methacrylate | 30 |
| Ethyl methacrylate | 70 |
| 2-hydroxyethyl-p-toluidine | 1.0 |
| 2-hydroxy-4-methoxybenzophenone | 2.0 |
| Butylated hydroxytoluene | 0.1 |
| Powder: | |
| Same as in Example 5. | |
| Powder-to-Resin ratio: | 3.5:1.0 |

Cure shrinkage was 0.63%.

EXAMPLE 7

|  | Parts by Weight |
|---|---|
| Liquid Resin: | |
| Tetrahydrofurfuryl methacrylate | 56 |
| Ethyl methacrylate | 85 |
| N,N-3,5-tetramethyl aniline | 1.0 |
| Butylated hydroxytoluene | 0.14 |
| Powder: | |
| Same as in Example 5 | |
| Powder-to-Resin ratio: | 3.5:1.0 |

For two specimens, shrinkage upon cure was 0.82% and 0.88%.

EXAMPLE 8

Same as Example 7, but with N,N-3,5-tetramethyl aniline at 2.0 parts.

Cure shrinkages for two specimens were 0.74% and 0.78%.

EXAMPLE 9–12

Same as Example 8, but with powder-to-resin ratios at:

| Example | 9 | 10 | 11 | 12 |
|---|---|---|---|---|
| Powder:Resin | 2:1 | 3:1 | 4:1 | 5:1 |
| Cure Shrinkage % | 1.33 | 0.50 | 0.51 | 0.59 |

-continued

| Example | 9 | 10 | 11 | 12 |
|---------|---|----|----|------|
|         |   |    |    | 0.53 |

EXAMPLE 13

| | Parts by Weight |
|---|---|
| Liquid Resin: | |
| Ethyl methacrylate | 40 |
| Tetrahydrofurfuryl methacrylate | 60 |
| 2-hydroxy-4-methoxybenzophenone | 2.0 |
| 2-hydroxyethyl-p-toluidine | 2.0 |
| Powder: | |
| Poly (ethyl methacrylate) with 1.5% benzoyl peroxide | 70 |
| Ray-Sorb T-2000 Barium glass coated with 1.5% A-174 silane | 30 |
| Powder-to-Resin ratio: | 4:1 |

Cure shrinkages in two specimens was 0.58% and 0.53%.

EXAMPLE 14

| | Parts by Weight |
|---|---|
| Liquid Resin: | |
| Ethyl methacrylate | 34.83 |
| Tetrahydrofurfuryl methacarylate | 52.25 |
| Ethoxylated bisphenol A dimethacrylate | 9.68 |
| Butylated hydroxytoluene | 0.10 |
| 2-hydroxyethyl-p-toluidine | 1.12 |
| 2-hydroxy-4-methoxybenzophenone | 1.94 |
| Powders: | |
| Poly (ethyl methacrylate) with added 1.5% benzoyl peroxide | 70 |
| Kimble Ray-Sorb T-2000 | 30 |
| Powder-to-Resin ratio: | 3.5:1.0 |

This gave excellent results. It is radiopaque, set in 5 minutes, become rubbery in about 1½ minutes and stays rubbery until nearly 5 minutes.

EXAMPLE 15–23

| | Parts by Weight |
|---|---|
| Liquid Resin: | |
| Part 1 | |
| Ethyl methacrylate | 40 |
| Tetrahydrofurfuryl methacrylate | 60 |
| 2-hydroxy-4-methoxybenzophenone | 2.0 |
| Butylated hydroxytoluene | 0.1 |
| 2-hydroxyethyl-p-toluidine | 1.0 |
| Part II | |
| Ethoxylated bisphenol A dimethacrylate | 100 |
| 2-hydroxy-4-methoxybenzophenone | 2.0 |
| Butylated hydroxytoluene | 0.1 |
| 2-hydroxyethyl-p-toluidine | 2.0 |
| Powder: | |
| Same as Example 13. | |
| Powder-to-Resin ratio | 3.5:1.0 |

| Example | Liquid Resin Ratio of A:B | Stringy | Rubbery | Hard |
|---------|---------------------------|---------|---------|------|
| 15 | 1/9 | 200 sec |     | 220 sec |
| 16 | 2/8 | 200     |     | 230 |
| 17 | 3/7 | 170     |     | 185 |
| 18 | 4/6 | 80      | 180 | 210 |
| 19 | 5/5 | 80      | 175 | 255 |
| 20 | 6/4 | 80      | 135 | 265 |
| 21 | 7/3 | 55      | 100 | 273 |
| 22 | 8/2 | 70      | 100 | 280 |
| 23 | 9/1 | 60      | 135 | 345 |

EXAMPLE 24

| | Parts by Weight |
|---|---|
| Liquid Resin: | |
| Ethyl methacrylate | 36 |
| Tetrahydrofurfuryl methacrylate | 54 |
| Ethoxylated bisphenol A dimethacrylate | 10 |
| Butylated hydroxytoluene | 0.10 |
| 2-hydroxyethyl-p-toluidine | 1.25 |
| 2-hydroxy-4-methoxybenzophenone | 2.0 |
| Powder: | |
| Poly (ethyl methacrylate) with 1.5% benzoyl peroxide | 70 |
| Ray-Sorb T-2000 | 30 |
| A-174 Silane | 0.45 |
| Powder-to-Resin ratio: | 3.5:1.0 |

Excellent. Becomes rubbery within two minutes and cures hard in 3½ to 4 minutes.

The benzoyl peroxide can be used at quantities from about 0.1% to about 5%. As the tertiary amine contact decreases, the peroxide should increase.

The butylated hydroxytoluene can be used in amounts from about 0.01 to about 1.0%. Other usable antioxidants include:

Hydroquinone at about 0.1 to about 2.5%

Methyl ether of hydroquinone at about 0.1 to about 5%.

Other usable accelerators may include:

N,N-3,5-tetramethylaniline at about ½ concentration of 2-HEPT.

N,N-dimethyl-p-toluidine at about ¼-½ concentration of 2-HEPT.

As stated before, the material has been found to be non-irritative to the gingival tissue, which is very important, and it has excellent stability with virtually no shrinkage on curing, as will be shown below. This enables it to remain in place for periods of even longer duration than are ordinarily expected for the laboratory to make the prosthesis. Its hardness is quite satisfactory. Its toughness enables it to be used for its purpose with very satisfactory results, although it can easily be removed in the same manner as other previously used materials. The fact that it is X-ray opaque means that it not only can be detected by X-ray but also that it will look normal in the mouth when its appearance must be relied upon.

CURE SHRINKAGE

A quick and reproduceable measurement of cure-shrinkage of polymeric dental restorative materials may be made with the aid of a quartz-tube dilatometer, such as that manufactured by Tinius-Olsen of Willow Grave, Pa. The device comprises a quartz tube into which a quartz rod is fitted. A fixture attached to the quartz tube enables positioning and locking of a dial indicator gage. A sample is placed into the bottom of the quartz tube, the quartz rod is placed atop the sample, and the dial gage is positioned to a mid-scale reading and locked. Any changes in sample length are recorded with an accuracy of 0.001 mm.

For this study, the samples were placed inside of 3-ml. glass syringes, manufactured by MPL Corporation Chicago, IL. These syringes have a silicone-coated glass barrel, two end fixtures of polyethylene, and a silicone rubber plunger. The syringes were modified by removing the plunger and twisting off the rear polyethylene closure.

The following test procedure was employed:
(1) Enough material was mixed to fill a syringe to a depth of approximately 10 mm. In practice, some trial and error may be required to determine the correct amount.
(2) The mixed material was quickly inserted into the syringe from the back.
(3) The plunger was inserted, and the syringe aspirated, as if it were filled with an injectable material.
(4) A plastic tip cap was screwed onto the ferrule.
(5) The assembly was dropped, tip first, into the quartz rod inserted to rest on the syringe plunger.
(6) The dial indicator was adjusted to give an intermediate reading and was locked. The initial reading was recorded.
(7) The dial reading was recorded every minute until it became constant. The final reading was substracted from the initial reading.
(8) The front closure was removed from the syringe and the cured polymer extracted from the syringe and its length measured.
(9) A percent shrinkage was calculated as follows:

$$\frac{\Delta \text{ length}}{\text{cured length}} \times 100 = \% \text{ linear shrinkage}$$

Since the syringe barrels are silicone coated, the curing material shrinks away from the barrel, so that only linear shrinkage is measured. This is, of course, quite adequate for comparing various materials of the same general type.

TEST RESULTS

A series of tests were run as described above comparing the cure shrinkage of the material of this invention to two other well-known materials sold for the fabrication of provisional crowns and bridges. Their manufactures claim that these materials have low cure shrinkage. Results are tabulated below:

|  | Material of this inventor | 1st competing material | 2nd competing material |
| --- | --- | --- | --- |
| Linear Cure Shrinkage, % | 0.41 | 1.54 | 0.38 |
| Shrinkage, % | 0.58 | 1.60 | 0.37 |
| Shrinkage, % | 0.63 | | |
| Shrinkage, % | 0.58 | | |
| Shrinkage, % | 0.53 | | |
| Average | 0.55 | 1.57 | 0.37 |
| Standard Deviation | 0.08 | 0.04 | 0.01 |

The data presented above allows the conclusion to be drawn that the material of this invention has a cure shrinkage better than one and nearly as good as the other competing material tested. Both of these other materials, however, tend to result in gingival reactivity.

To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

We claim:
1. A provisional crown-and-bridge resin comprising: a liquid resin component and a powder component, said liquid resin component containing tetrahydrofurfuryl methacrylate as a major ingredient and being free from methyl methacrylate and also containing an anti-oxidant and an accelerator,
said powder component containing poly (ethyl methacrylate) as a major ingredient and a curing agent for the resin component,
said powder being mixed with said resin shortly before application at a ratio of about two to about five parts of powder to one part of liquid resin by weight, to give a suitably flowing mixture.

2. The provisional crown-and-bridge resin of claim 1, wherein said resin component also contains ethyl methacrylate as a major ingredient.

3. The provisional crown-and-bridge resin of claim 2 wherein said resin component also contains ethoxylated bisphenol A dimethacrylate as a major component.

4. The provisional crown-and-bridge resin of claim 1 wherein said powder includes a substantial proportion of amorphous silica.

5. The provisional crown-and-bridge resin of claim 1 wherein said powder incorporates a substantial amount of X-ray opaque barium glass.

6. A provisional crown-and-bridge resin comprising:
a liquid resin component, containing as its major ingredients ethyl methacrylate and tetrahydrofurfuryl methacrylate and, as minor ingredients, an anti-oxidant and a cure accelerator, and,
a powder component, containing as its major ingredients poly (ethyl methacrylate) and X-ray opaque filler and, as a minor ingredient, a curing agent for said liquid resin component,
said resin and powder components being mixed to a desired consistency with the powder present in amounts by weight from about two to about five times the amount by weight of the resin.

7. The resin of claim 6 having, as a minor ingredient of the liquid resin component, an ultra-violet-light absorbing material.

8. A provisional crown-and-bridge resin comprising an intimate mixture of:
a liquid resin component containing as its major ingredient a blend of ethyl methacrylate, tetrahydrofurfuryl methacrylate, and ethoxylated bisphenol A dimethacrylate, and, as minor ingredients an anti-oxidant and a cure accelerator, and
a powder component having as its principal ingredient poly (ethyl methacrylate) and, as a minor ingredient, a curing agent for the liquid resin component,
the powder component being present in an amount of about two to about five times as much, by weight, as the liquid resin component.

9. The provisional crown-and-bridge resin of claim 8 wherein the powder component also includes a substantial amount of barium glass.

10. The provisional crown-and-bridge resin of claim 8 wherein the powder compound also includes a substantial amount of amorphous silica.

11. The provisional crown-and-bridge resin of claim 8 wherein said liquid resin compound also includes an ultra-violet-light absorbing agent.

12. A provisional crown-and-bridge resin consisting essentially of a liquid resin component and a powder component mixed to a desired consistency, said liquid resin consisting essentially of:

| Ingredient | Parts by weight |
|---|---|
| Ethyl methacrylate | 0–70.0 |
| Ethoxylated bisphenol A dimethacrylate | 40.0 |
| Tetrahydrofurfuryl methacrylate | 60.0 |
| Anti-oxidant | sufficient to prevent oxidation |
| Cure accelerator | as desired | said powder component consisting essentially of:

| Ingredient | Parts by Weight |
|---|---|
| Poly (ethyl methacrylate) | 39–100 |
| Amorphous silica | 0–39 |
| Curing agent | enough to cure the curable resin in liquid resin component |

13. The provisional crown-and-bridge resin of claim 12 wherein said anti-oxidant is chosen for the group consisting of:

| Ingredient | Parts by Weight |
|---|---|
| Butylated hydroxytoluene | 0.01 to 1.0 |
| Hydroquinone | 0.1 to 2.5 |
| Methyl ether of hydroquinone | 0.1 to 5.0 |

14. The provisional crown-and-bridge resin of claim 12 wherein the cure accelerator is chosen for the group consisting of:

| Ingredient | Parts by Weight |
|---|---|
| 2-hydroxyethyl-p-toluidine | 0.3 to 1.94 |
| N,N-3,5-tetramethylaniline | 0.15 to .97 |
| N,N-dimethyl-p-toluidine | 0.07 to .97 |

15. The provisional crown-and-bridge resin of claim 12 wherein the curing agent is benzoyl peroxide at quantities from about 0.17% to about 5%, the amount increasing with decrease in the amount of tertiary amine in the liquid resin.

16. The provisional crown-and-bridge resin of claim 12 containing an effective amount of ultra-violet-light absorbing agent.

17. The provisional crown-and-bridge resin of claim 16 wherein said absorbing agent is 2-hydroxy-4-methoxybenzophenone, up to 2.0 parts by weight.

18. A provisional crown-and-bridge resin, consisting essentially of a liquid resin component consisting essentially of:

| Ingredient | Parts by Weight |
|---|---|
| Tetrahydrofurfuryl methacrylate | 60 |
| Ethoxylated bisphenol A dimethacrylate | 40 |
| Butylated hydroxytoluene | 0.1 |
| 2-hydroxy-4-methoxybenzophenone | 2.0 |
| 2-hydroxyethyl-p-toluidine | 2.0 | and a powder component consisting essentially of poly (ethyl methacrylate) with 1.5% benzoyl peroxide, the powder-to-resin ratio being about 3.5:1.0.

19. A provisional crown-and-bridge resin, consisting essentially of a liquid resin component consisting essentially of:

| Ingredient | Parts by Weight |
|---|---|
| Tetrahydrofurfuryl methacrylate | 60 |
| Ethoxylated bisphenol A dimethacrylate | 40 |
| Butylated hydroxytoluene | 0.1 |
| 2-hydroxy-p-toluidine | 1.0 |
| 2-hydroxy-4-methoxybenzophenone | 2.0 | and a powder component consisting essentially of poly (ethyl methacrylate) with 1.5% benzoyl peroxide, the powder-to-resin ratio being about 3.5:1.0.

20. A provisional crown-and-bridge resin, consisting essentially of a liquid resin component consisting essentially of:

| Ingredient | Parts by Weight |
|---|---|
| Tetrahydrofurfuryl methacrylate | 60 |
| Ethyl methacrylate | 40 |
| Butylated hydroxytoluene | 0.1 |
| 2-hydroxy-4-methoxybenzophenone | 2.0 |
| 2-hydroxyethyl-p-toluidine | 1.0 | and a powder component consisting essentially of:

| Ingredient | Parts by Weight |
|---|---|
| Poly (ethyl methacrylate) with 1.5% benzoyl peroxide | 50 |
| a 90 to 10 mixture of poly (ethyl methacrylate) and poly (methyl methacrylate) without added benzoyl peroxide | 50, |
| the powder-to-resin ratio being about | 3.5:1.0. |

21. A provisional crown-and-bridge resin, consisting essentially of a liquid resin component consisting essentially of:

| Ingredient | Parts by Weight |
|---|---|
| Tetrahydrofurfuryl methacrylate | 40 |
| Ethyl methacrylate | 60 |
| 2-hydroxyethyl-p-toluidine | 0.5 | and a powder component consisting essentially of:

| Ingredient | Parts by Weight |
|---|---|
| Poly (ethyl methacrylate) with 1.5% benzoyl peroxide | 50 |
| a 90 to 10 mixture of poly (ethyl methacrylate) and poly (methyl methacrylate) without added benzoyl peroxide | 50, | the powder-to-resin ratio being about 3.5:1.0.

22. A provisional crown-and-bridge resin, consisting essentially of a liquid resin component consisting essentially of:

| Ingredient | Parts by Weight |
|---|---|
| Tetrahydrofurfuryl methacrylate | 50 |
| Ethyl methacrylate | 50 |
| 2-hydroxyethyl-p-toluidine | 0.3 |
| 2-hydroxy-4-methoxybenzophenone | 2.0 | and a powder component consisting essentially of poly (ethyl methacrylate) with 1.5% added benzoyl peroxide, the powder-to-resin ratio being about 3.5:1.0.

23. A provisional crown-and-bridge resin, consisting essentially of a liquid resin component consisting essentially of:

| Ingredient | Parts by Weight |
|---|---|
| Tetrahydrofurfuryl methacrylate | 30 |
| Ethyl methacrylate | 70 |
| 2-hydroxyethyl-p-toluidine | 1.0 |
| 2-hydroxy-4-methoxybenzophenone | 2.0 |
| Butylated hydroxytoluene | 0.1 | and a powder component consisting essentially of poly (ethyl methacrylate) with 1.5% added benzoyl peroxide,
  the powder-to-resin ratio being about 3.5:1.0.

24. A provisional crown-and-bridge resin, consisting essentially of a liquid resin component consisting essentially of:

| Ingredient | Parts by Weight |
|---|---|
| Tetrahydrofurfuryl methacrylate | 56 |
| Ethyl methacrylate | 85 |
| N,N-3,5-tetramethyl aniline | 1.0 |
| Butylated hydroxytoluene | 0.14 | and a powder component consisting essentially of poly (ethyl methacrylate) with 1.5% added benzoyl peroxide,
  the powder-to-resin ratio being about 3.5:1.0.

25. A provisional crown-and-bridge resin, consisting essentially of a liquid resin component consisting essentially of:

| Ingredient | Parts by Weight |
|---|---|
| Tetrahydrofurfuryl methacrylate | 56 |
| Ethyl methacrylate | 85 |
| N,N-3,5-tetramethyl aniline | 2.0 |
| Butylated hydroxytoluene | 0.14 | and a powder component consisting essentially of poly (ethyl methacrylate) with 1.5% added benzoyl peroxide,
  the powder-to-resin ratios from about 2:1 to about 5:1.

26. A provisional crown-and-bridge resin, consisting essentially of a liquid resin component consisting essentially of:

| Ingredient | Parts by Weight |
|---|---|
| Ethyl methacrylate | 40 |
| Tetrahydrofurfuryl methacrylate | 60 |
| 2-hydroxy-4-methoxybenzophenone | 2.0 | and a powder component consisting essentially of:

| Ingredient | Parts by Weight |
|---|---|
| Poly (ethyl methacrylate) with 1.5% benzoyl peroxide | 70 |
| Barium glass coated with silane | 30, | the powder-to-resin ratio being about 4:1.

27. A provisional crown-and-bridge resin, consisting essentially of a liquid resin component consisting essentially of:

| Ingredient | Parts by Weight |
|---|---|
| Ethyl methacrylate | 34.83 |
| Tetrahydrofurfuryl methacrylate | 52.25 |
| Ethoxylated bisphenol A dimethacrylate | 9.68 |
| Butylated hydroxytoluene | 0.10 |
| 2-hydroxyethyl-p-toluidine | 1.12 |
| 2-hydroxy-4-methoxybenzopherine | 1.94 | and a powder component consisting essentially of:

| Ingredient | Parts by Weight |
|---|---|
| Poly (ethyl methacrylate) with added benzoyl peroxide | 70.0 |
| Barium glass coated with silane | 30.0 | the powder-to-resin ratio being about 3.5:1.0.

28. A provisional crown-and-bridge resin, consisting essentially of a liquid resin component consisting essentially of:

| Ingredient | Parts by Weight |
|---|---|
| Part I | |
| Ethyl methacrylate | 40 |
| Tetrahydrofurfuryl methacrylate | 60 |
| 2-hydroxy-4-methoxybenzophenone | 2.0 |
| Butylated hydroxytoluene | 0.1 |
| 2-hydroxyethyl-p-toluidine | 1.0 |
| Part II | |
| Ethoxylated bisphenol A dimethacrylate | 100.0 |
| 2-hydroxy-4-methoxybenzophenone | 2.0 |
| Butylated hydroxytoluene | 0.1 |
| 2-hydroxyethyl-p-toluidine | 2.0 | the ratio of Part I and Part II lying in the range of 1:9 to 9:1,
  and a powder component consisting essentially of:

| Ingredient | Parts by Weight |
|---|---|
| Poly (ethyl methacrylate) with 1.5% benzoyl peroxide | 70 |
| Barium glass coated with silane | 30 | the powder-to-resin ratio being about 3.5:1.0.

29. A provisional crown-and-bridge resin, consisting essentially of a liquid resin component consisting essentially of:

| Ingredient | Parts by Weight |
|---|---|
| Ethyl methacrylate | 36 |
| Tetrahydrofurfuryl methacrylate | 54 |
| Ethoxylated bisphenol A dimethacrylate | 10 |
| Butylated hydroxytoluene | 0.10 |
| 2-hydroxyethyl-p-toluidine | 1.25 |
| 2-hydroxy-4-methoxybenzophenone | 2.0 | and a powder component consisting essentially of:

| Ingredient | Parts by Weight |
|---|---|
| Poly (ethyl methacrylate) with 1.5% benzoyl peroxide | 70 |
| Barium glass | 30 |
| Silane | 0.45 | the powder-to-resin ratio being about 3.5:1.0.

* * * * *